United States Patent [19]

Conti

[11] Patent Number: 5,059,685

[45] Date of Patent: Oct. 22, 1991

[54] CATIONIZED POLYSACCHARIDE DERIVATIVES WITH HYPOCHOLESTEROLEMIC ACTIVITY

[75] Inventor: Franco Conti, Milan, Italy

[73] Assignee: Etablissement Texcontor, Liechtenstein, Italy

[21] Appl. No.: 652,217

[22] Filed: Feb. 5, 1991

Related U.S. Application Data

[63] Continuation of Ser. No. 249,124, Sep. 26, 1988, abandoned.

[30] Foreign Application Priority Data

Nov. 20, 1987 [IT] Italy .................. 22711 A/87

[51] Int. Cl.$^5$ .................. C07H 1/00; C07H 5/00; C08B 37/00; C08B 31/00

[52] U.S. Cl. .................. 536/1.1; 536/17.2; 536/17.9; 536/18.5; 536/18.7; 536/20; 536/30; 536/22; 536/45; 536/52; 536/55; 536/55.2; 536/55.3

[58] Field of Search .............. 536/1.1, 17.2, 17.9, 536/18.5, 18.7, 20, 22, 30, 45, 52, 55, 55.2, 55.3

[56] References Cited

U.S. PATENT DOCUMENTS

| | | | |
|---|---|---|---|
| 4,129,722 | 12/1978 | Iovine et al. | 536/43 |
| 4,330,533 | 5/1982 | Takayama et al. | 514/54 |
| 4,411,891 | 10/1983 | Mizutani et al. | 536/51 |
| 4,436,731 | 3/1984 | Maltz | 514/55 |
| 4,663,159 | 5/1987 | Brode, II et al. | 536/90 |
| 4,772,690 | 9/1988 | Lang et al. | 536/20 |
| 4,921,949 | 5/1990 | Lang et al. | 536/20 |

FOREIGN PATENT DOCUMENTS

| | | |
|---|---|---|
| 0010299 | 9/1980 | European Pat. Off. |
| 0066135 | 12/1982 | European Pat. Off. |
| 0212145 | 3/1987 | European Pat. Off. |
| 5345 | 10/1967 | France |

OTHER PUBLICATIONS

Patent Abstracts of Japan, vol. 10, No. 226 (Aug. 7, 1986).

Chemical Abstracts, vol. 109, Abstract No. 204924h (Dec. 5, 1988).

*Primary Examiner*—Ronald W. Griffin
*Assistant Examiner*—Everett White
*Attorney, Agent, or Firm*—Parkhurst, Wendel & Rossi

[57] ABSTRACT

Cationized derivatives of natural polysaccharides having a polyglucoside structure with 50–5000 monomer units and one or more side chains bonded to the glucoside nucleus by a nitrogen or oxygen atom or an amide group, said side chains having one or more quaternary nitrogen atoms so that each monomer unit has a cation charge density exceeding two. The new compounds are particularly active as hypocholesterolemic agents.

7 Claims, No Drawings

CATIONIZED POLYSACCHARIDE DERIVATIVES WITH HYPOCHOLESTEROLEMIC ACTIVITY

This is a continuation of application Ser. No. 07/249,124 filed Sept. 26, 1988, now abandoned.

A. TECHNICAL FIELD

This invention relates to cationized derivatives of natural polysaccharides possessing hypocholesterolemic activity.

The term "cationized" signifies the presence in the molecule of quaternary nitrogen atoms, thus having a positive charge, which allow salification with acid anions.

In the compounds of the invention the quaternary nitrogen atoms are salified with acids which are pharmaceutically acceptable in the consideration of their hypocholesterolemic use.

B. THE TECHNICAL PROBLEM

Compounds with hypocholesterolemic activity must possess various properties, such as stability in the gastrointestinal tract, no steric impediment which renders the reaction between the bile acids and the reactive groups of the compound difficult, and a good reaction rate with the bile acids so as to prevent their excretion from the body without having completed their blocking action, with consequent acid elimination.

This latter property is very important because it enables a higher reduction in the body cholesterol to be obtained for equal quantities of compound administered and equal theoretical blocking capacity.

C. PRIOR ART

Various products with hypocholesterolemic activity are known, such as certain ion exchange resins.

These polymers are however insoluble in water and their capacity for blocking bile acids is therefore low, in addition to the undesirable side effects which they produce. Chitosan derivatives with positive charges in the molecule are also known (M. Sugano, T. Fujikawa et al. Am. J. of Clinical Nutrition, 33, April 1980, pp 787-793). In these compounds the positive charges on the chitosan polysaccharide macromolecules are obtained by simple protonization of the amino group, so that under the pH conditions of the intestinal tract (pH≈7.2) the proton is almost completely removed, as the chitosan pKa is 6.3. For this reason, the capacity of the polymer to interact with the bile salts is very low.

The present applicant has described cationized derivatives of natural polysaccharides with hypocholesterolemic properties in two of his previous patents (U.S. Pat. No. 4,436,731 and EP-A-0212145).

Both these patents describe products with no side chains or with only one quaternary nitrogen atom for each side chain bonded to the glucoside nucleus of the polymeric molecule. The products described in the two patents have good hypocholesterolemic activity which is better than previously known compounds, and they are very well tolerated by the body.

D. DETAILED DESCRIPTION OF THE INVENTION

It has now been surprisingly found, in accordance with the present invention, that if a natural polysaccharide has a number of cationized side chains, or more than one quaternary nitrogen atom in the same chain so that each monomer unit has a cation charge density equal or greater than two, the hypocholesterolemic activity of said polysaccharide is considerably greater than if the quaternary nitrogen atoms are present in such a quantity that the cation density per monomer unit is less than two.

The hypocholesterolemic activity of a natural polysaccharide with cationized side chains is therefore more influenced by the cation charge density of the individual monomer unit than by the total number of quaternary nitrogen atoms present in the molecules.

Without wishing to be bound to a particular interpretation of the phenomenon, it is thought that the charge density influences the kinetics of the reaction between the bile acids and the cationized polysaccharide, thus resulting in a greater bile acid blocking rate and a consequent improved elimination thereof.

The present invention therefore relates to cationized derivatives of natural polysaccharides having one or more side chains bonded to the glucoside nucleus by a nitrogen or oxygen atom or an amide group, each of said side chains having a number of quaternary nitrogen atoms such that each monomer unit has a cation charge density greater than two.

The degree of substitution of the glucoside nucleus of the cationized derivatives according to the invention varies from 0.5 to 2. The degree of substitution signifies the ratio of the number of cationized side chains to the number of monomer units of the polysaccharide.

Thus, the cationized derivatives of the present invention can be represented by the general formula

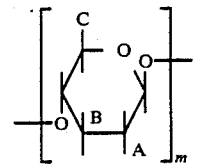

in which
m is a whole number between 50 and 5000;
A signifies:
$N^{(+)}RR^1R^2$; $-NR-CO-R^3$; $-NR-R^3-N-R-CO-CH(R^4)-(CH_2)_n-R^4$;
$NR-R^5$;
$NR-CO-CH(R^4)-(CH_2)_n-NR-C(NH)R^4$;
$NR-CH_2-CH(OH)-(CH_2)_n-Ar-(CH_2)_n-N^{(+)}RR^1R^2$;
where n is a whole number between 0 and 20;
R, $R^1$ and $R^2$, which can be the same or different, signify hydrogen, a linear or branched alkyl radical with 1-30 carbon atoms, phenyl or an alkylphenyl radical with 7-30 carbon atoms;
$R^3$ signifies $-CH_2-CH(OH)-(CH_2)_n-N^{(+)}RR^1R^2$;
$R^4$ signifies $-NR-R^3$;
$R^5$ signifies

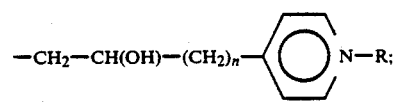

Ar signifies phenyl, or an alkylphenyl radical with 7-30 carbon atoms;
B signifies:

OR or $R^3$ where R and $R^3$ have the same meanings as for A;

C signifies:
—$CH_2OH$; —$CH_2OR$; —COOH; —COOR; —$CH_2$—$R^3$; —CO—NR—$(CH_2)_n$—NR—$R^3$; where R, $R^3$, n have the aforesaid meanings, with the proviso that if R is hydrogen $R^1$ and $R^2$ are not hydrogen and for each cationized nitrogen atom (i.e. shown as tetravalent in the formula) there exists one anion X of a pharmaceutically acceptable acid, in particular X signifying Cl—, Br—, I—, $HSO_4$—, $CH_3OSO_3$—, $NO_3$—, $EtOSO_3$—.

It is apparent that polysaccharides can be obtained with a single side chain having two or more quaternary nitrogen atoms, or with two or three side chains attached to the same glucoside nucleus, or other similar combinations, provided that the resultant cation charge density for each monomer unit is equal or greater than 2.

In the preferred embodiments of the invention there are at least two quaternary nitrogen atoms in the same side chain.

The polysaccharides preferably used to obtain the compounds of the present invention are: starch, cellulose, chitosan, tragacanth, guar gum, carob meal and tamarind.

The starting polysaccharides used are pretreated both to reduce their molecular complexity and in particular to increase their reactivity and thus simplify the introduction of the side chains and their cationization.

The pretreatment of the starting polysaccharide consists of partial hydrolyzation to reduce its molecular weight, and/or solubilization in a suitable solvent with reprecipitation in an amorphous form which is very reactive even if the subsequent reactions for introducing the side chains are conducted in heterogeneous phase.

If the starting polysaccharides are water-soluble, such as starch, pretreatment is effected with a 10–30% alkaline hydroxide solution, preferably sodium hydroxide, at ambient temperature, for a time of 1–3 hours.

If the starting polysaccharides are insoluble in water, such as chitosan or cellulose, pretreatment is effected by treating them under reflux for a time of 10–30 hours with 0.01–10M formic, acetic or hydrochloric acid solutions.

The pretreatment can also include oxidising a primary alcohol group of the glucoside nucleus to carboxyl with consequent transformation of the polysaccharide into a polyurethonic acid.

The subsequent introduction of the side chains and their cationization is effected in an organic solvent which dissolves or swells the pretreated polysaccharide. The preferred solvents, both for the pretreatment and the subsequent reactions, are aliphatic alcohols, in particular those having 1–4 carbon atoms; polyalcohols with 2–8 carbon atoms, in particular ethylene and diethylene glycol and glycerin; aliphatic ketones, in particular acetone; linear and cyclic ethers, in particular dioxane; and aliphatic and aromatic hydrocarbons with 6–15 carbon atoms.

The reactions for introducing side chains into the glucoside nucleus of the pretreated polysaccharide are effected by using as preferred reagents the aliphatic and/or aromatic amines or the amino acids having the structure which it is intended to introduce into the polysaccharide molecules as side chain.

The quaternary nitrogen atoms are introduced into the side chains by reactions using quaternary ammonium salts having equal or different nitrogen substituents and having a reactive epoxide group.

Typically, the pretreated polysaccharide is suspended in the solvent system under agitation for at least one hour, then centrifuged or filtered. This operation is repeated until the solvent used in the pretreatment and in the introduction of the one or more side chains has exchanged as completely as possible with that used for the quaternization process. In all cases, the water content of the product is less than 5% by weight.

Depending on the starting polysaccharide and/or on the side chains introduced, the cationization reaction is conducted either in suspension or in solution in the chosen solvent system. The normally used suspension has a solids content typically exceeding 10%. The reaction time is typically between 1 and 20 hours and the temperature between 50° and 150° C. The molar ratio of treated polysaccharide to cationization agent varies from 1:2 to 1:6.

Using the various combinations of reaction time, temperature and molar ratio it is possible to obtain products with levels of substitution within the desired limits. The methods used for separating, purifying and recovering the final product include extraction, centrifuging and/or filtration, and solvent washing in accordance with the normal techniques of organic synthesis.

The side chain introduction and cationization can be repeated to obtain several side chains, or to lengthen those already connected to the glucoside nucleus by spacing apart the quaternary nitrogen atoms inserted into one and the same chain.

In the preferred embodiments of the invention, there is a distance of at least three C atoms between two quaternary nitrogen atoms inserted into one and the same chain.

EXAMPLE 1

Preparation of L-lysine chloride dihydrochloride 100 g of lysine dihydrochloride are suspended in 500 ml of methylene chloride, the suspension then being cooled to 0° C.

70.0 g of thionyl chloride are then added and the system is left to react for 3 hours. 102.8 g of the corresponding acyl chloride are obtained (yield 95%); elementary analysis gives C=30.10%, H=6.20%, N=11.50%, Cl=44.5%.

The L-lysine chloride dihydrochloride is then condensed with chitosan and reacted with glycidyl-trimethyl-ammonium chloride as follows:

The L-lysine chloride dihydrochloride is suspended in 500 ml of methylisobutyl ketone and 75.0 g of chitosan are added in continuation. The mixture is heated to 50° C. for 3 hours to obtain 85.2 g of chitosan-N-acyl-lysine dihydrochloride (yield 50%). The product is filtered and washed with methanol, neutralised with $NH_4OH$ and treated in isopropanol with 250 g of glycidyl-trimethyl-ammonium chloride for 16 hours at 80° C. 142.0 g of product are obtained (yield 75%) as a 15% solution.

EXAMPLE 2

Polygalacturonic acid-hexamethylenediamine-glycidyltrimethyl-ammonium chloride derivatives 100 g of polygalacturonic acid are suspended in 200 ml of MeOH. 100 g of dicyclohexylcarbodiimide (DCC) and 350 g of hexamethylenediamine are added and the mixture heated under reflux for 16 hours.

On filtration, 120.5 g of polygalacturonic acid-hexamethylenediamine monocondensation product are obtained (yield 80%; N=9%).

The solid obtained is again suspended in methanol and 200.0 g of glycidyltrimethyl-ammonium chloride added, and the mixture heated under reflux for 16 hours. The product is filtered off and washed with a little methanol.

Yield 80%;

Elementary analysis C=51%; H=9%; N=9.0%; Cl=7.5% equivalent to $2.1 \times 10^{-3}$ meq/g of cationic heads.

EXAMPLE 3

100 g of chitosan (degree of deacetylation 80%) are suspended in 250 ml of a 30% w/v solution of NaOH and heated to 50° C. for 16 hours in a stream of nitrogen. The suspension is filtered and the product washed with a 1:1 methanol-water mixture until pH 7.5-8.0.

The chitosan treated in this manner is suspended in 300 ml of isopropanol and 500 g of glycidyltrimethylammonium chloride (GTAC) are added. The treatment is prolonged for 6 hours at 80° C.

The mixture is cooled and HCl is added until neutral. 310.5 g of product are obtained with a molar yield of 85%. (Cl=14.6%; N=6.0%).

EXAMPLE 4

100 g of chitosan (5.9 meq/g free amino groups) are suspended in 0.5 liters of isopropanol and treated with 130.0 g of a 40% formalin solution and 100 g of an 80% HCOOH solution at 80° C. for 8 hours. In this manner 95.5 g of dimethylated product are obtained (yield 85% by weight) characterised by NMR: The product (98.5 g) is then suspended in 0.5 l of DMF (dimethylformamide) and left stirring for 16 hours at ambient temperature, after which the temperature is raised to 80° C. and 225 g of glycidyltrimethylammonium chloride are added and the mixture left to react for 8 hours.

It is allowed to cool and a solution of HCl in methanol is added until resultant acidity obtained. It is then filtered and the product washed several times with methanol.

195.5 g obtained; overall yield 85%.

Elementary analysis: C=44.2%; H=7.3%; N=5.5%; Cl=14.6% equivalent to $4.1 \times 10^{-3}$ meq/g of cationic heads.

The product obtained has the structural formula

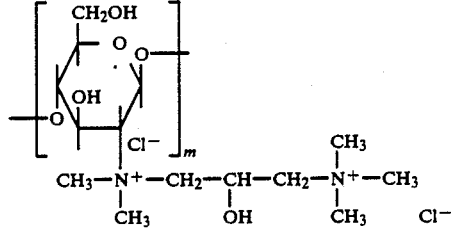

as determined by NMR analysis.

EXAMPLE 5

100.0 g of chitosan (5.7 meq/g free amino groups) are suspended in 0.5 liters of dimethylformamide for 16 hours while stirring at ambient temperature. 340.0 g of 1-bromo-2,2'-dihydroxymethyl-3-propanol and 105.0 g of tributylamine are then added.

The mixture is left to react for 24 hours at 80° C., after which it is cooled by adding 0.5 l of methanol, and filtered.

170.0 g of solid are obtained with a yield of 80%.

The product (tri-hydroxylated derivative) is then suspended in 1.0 l of isopropanol containing 5.0% of gaseous HCl. 275.0 g of glycidyltrimethylammonium chloride are then added, then heating to 80° C. for 16 hours. 298.8 g of water-soluble product are obtained with an overall yield of 70% calculated as free base.

Elementary analysis: C=45.5%; H=7.5%; N=5.1%; Cl=10.0% equivalent to $2.8 \times 10^{-3}$ meq/g of cationic heads.

The product obtained has the structural formula

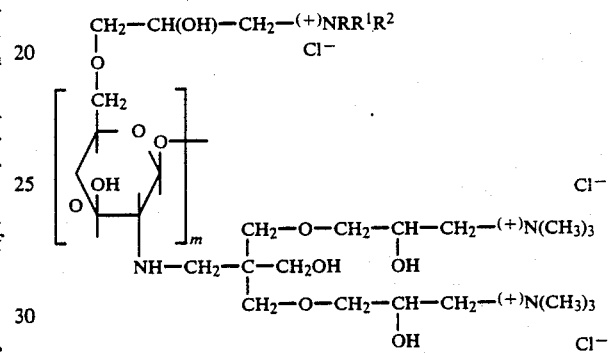

as determined by NMR analysis.

The products of the present invention were used in a series of pharmacological trials, the results of which are summarised in the tables given hereinafter. For comparison purposes the results obtained under the same conditions with the product ET 1020 derived from chitosan as described in European patent application 0212145 and having a single quaternary ammonium group per monomer unit are also given.

The following tests were used to demonstrate the "in vivo" hypocholesterolemic effect of the various products:

1) Effect on hypercholesterolemia induced by a cholesterol-enriched diet in the rat and rabbit;
2) Effect on fecal excretion of bile acids in the dog.

1) To induce hypercholesterolemia in rats, the animals were given a diet in accordance with Nath and coll. (J. Nutrit. 67, 289, 1959) containing:

| devitaminised casein | 20% |
| dl-methionine | 0.4% |
| Hegsted saline mixture | 4% |
| saccharose | 49.1% |
| cholesterol | 1% |
| cholic acid | 0.5% and vitamins |

To induce hypercholesterolemia in rabbits, 1 g/animal/day of cholesterol was administered by gastric probe.

Sprague-Dawley rats of 200 g average weight and New Zealand rabbits of 3 kg weight were used, divided into groups of 10 animals each.

All animals were rendered hypercholesterolemic by diet. One group was not treated and served as the control group, while the other groups were treated with 0.5 g/kg of the various products under examination for 30 days.

After 30 days all the animals were killed and the blood collected from the carotid arteries was tested for total plasmatic cholesterol (Pearson and coll. J. Chem. Endocrin. Metabolism 12, 1245, 1952).

2) To evaluate fecal excretion of bile acids 48 male beagle dogs were used of about 8 kg weight, divided into 12 groups of 4 animals each. All animals were kept under standard diet and stalling, and with the exception of one control group all the other groups were administered with 2 g/kg. day of one of the products under examination for 25 days, in addition to the diet.

26 days after commencement of the trial, the feces of the dogs, which had fasted for 12 hours in a metabolic cage, were tested for bile acids (Grundy and coll., J. Lipid res. 6, 397, 1965; Makita and coll., Ann. Biochem. 5, 523, 1963; Forman and coll., Clin. Chem. 14, 348, 1969).

Tables 1 and 2 summarise the results obtained in the rats and rabbits rendered hypercholesterolemic by diet and treated with the various products indicated. Table 3 shows the bile acid excretion from dogs treated with 2 g/kg day of the various products.

TABLE 1

Total serous cholesterol in rats subjected to Nath diet (Nath and coll. J. Nutrit. 67, 289, 1959) for 30 days and treated with the various products.

|  | Control | ET 1020 | ETA | ETB | ETC | ETD | ETE |
|---|---|---|---|---|---|---|---|
| No. rats | 10 | 10 | 10 | 10 | 10 | 10 | 10 |
| mg % | 328 | 121 | 94 | 98 | 83 | 86 | 79 |
|  | 37.4 | 12.6 | 10.1 | 9.4 | 7.5 | 8.9 | 7.1 |

TABLE 2

Total serous cholesterol in rabbits subjected to cholesterol-enriched diet for 30 days and treated with the various products.

|  | Control | ET 1020 | ETA | ETB | ETC | ETD | ETE |
|---|---|---|---|---|---|---|---|
| No. rats | 10 | 10 | 10 | 10 | 10 | 10 | 10 |
| mg % | 751 | 215 | 178 | 186 | 144 | 152 | 157 |
|  | 81.4 | 26.9 | 21.6 | 24.7 | 18.2 | 15.6 | 17.8 |

TABLE 3

Fecal bile acid excretion in dogs treated with the various products for 25 days.

|  | Control | ET 1020 | ETA | ETB | ETC | ETD | ETE |
|---|---|---|---|---|---|---|---|
| No. dogs | 4 | 4 | 4 | 4 | 4 | 4 | 4 |
| mcg/g of feces | 846 | 2680 | 2890 | 2940 | 3085 | 3040 | 3070 |
|  | 65.2 | 244.8 | 260.2 | 240.6 | 265.9 | 280.5 | 248.6 |

From these tables it is apparent that the cationized polysaccharide derivatives of the present invention show hypocholesterolemic activity exceeding that of analogous compounds with less than two cationic charges per monomer unit, both in rats and in rabbits subjected to a hypercholesterolemic diet.

The results of fecal excretion in the dog confirm the binding activity of the products of the invention on bile acids. In this respect, administering these products leads to a large increase in the quantity of bile acids excreted with the feces, this quantity being much higher than that obtained with analogous compounds with less than two cationic charges per monomer unit.

I claim:

1. A cationized derivative of natural polysaccharide with hypocholesterolemic activity of the formula:

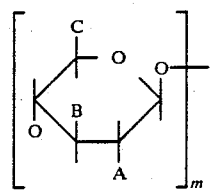

wherein
m is a whole number between 50 and 5,000;
A is
$N^{(+)}RR^1R^2$; $-NR-CO-R^3$; $-NR-R^3$;
$NR-CO-CH(R^4)-(CH_2)_n-R^4$; $-NR-R^5$;

$$NR-CO-CH(R^4)-(CH_2)_n-\underset{NH}{\overset{\|}{C}}-R^4; \text{ or}$$

$NR-CH_2-CH(OH)-(CH_2)_n-Ar-(CH_2)_n-N^{(+)}RR^1R^2$;

n is a whole number between 0 and 20;
R, $R^1$ and $R^2$ are the same or different and are hydrogen, a linear or branched alkyl with 1 to 30 carbon atoms, phenyl, or a $C_7-C_{30}$ alkylphenyl radical;
$R^3$ is $-CH_2-CH(OH)-(CH_2)_n-N^{(+)}RR^1R^2$;
$R^4$ is $-NR-R^3$;
$R^5$ is

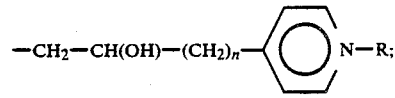

Ar is phenyl or a $C_7-C_{30}$ alkylphenyl radical;
B is OR or $R^3$ where R and $R^3$ have the same meanings as for A;
C is $-CH_2OH$; $-CH_2OR$; $-COOH$; $-COOR$; $-CH_2OR^3$; or $-CO-NR-(CH_2)_n-NR-R^3$ where R,$R^3$, and n are as defined previously, with the provisos that (1) if R is hydrogen, $R^1$ and $R^2$ are not hydrogen, (2) for each cationized nitrogen atom, there exists one anion X of a pharmaceutically acceptable acid, said anion selected from the group consisting of Cl—, Br—, I—, $HSO_4$—, $CH_3OSO_3$—, $NO_3$—, and $EtOSO_3$—, and (3) each of the side chains having a number of quaternary nitrogen atoms such that each monomer unit has a cationic charge density greater than or equal to two.

2. A process for preparing a cationized derivative of a natural polysaccharide of the formula:

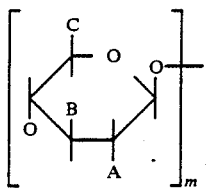

wherein m is a whole number between 50 and 5,000;

A is

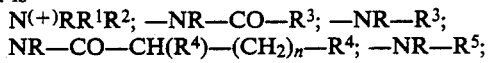

$NR-CO-CH(R^4)-(CH_2)_n-\underset{\underset{NH}{\|}}{C}-R^4$; or

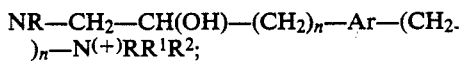

n is a whole number between 0 and 20;

R, $R^1$ and $R^2$ are the same or different and are hydrogen, a linear or branched alkyl with 1 to 30 carbon atoms, phenyl, or a $C_7$-$C_{30}$ alkylphenyl radical;

$R^3$ is $-CH_2-CH(OH)-(CH_2)_n-N^{(+)}RR^1R^2$;

$R^4$ is $-NR-R^3$;

$R^5$ is

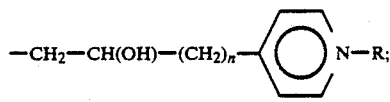

Ar is phenyl or a $C_7$-$C_{30}$ alkylphenyl radical;

B is OR or $R^3$ where R and $R^3$ have the same meanings as for A;

C is $-CH_2OH$; $-CH_2OR$; $-COOH$; $-COOR$; $-CH_2OR^3$; or $-CO-NR-(CH_2)_n-NR-R^3$ where R, $R^3$, and n are as defined previously, with the provisos that (1) if R is hydrogen, $R^1$ and $R^2$ are not hydrogen, (2) for each cationized nitrogen atom, there exists one anion X of a pharmaceutically acceptable acid, said anion selected from the group consisting of $Cl^-$, $Br^-$, $I^-$, $HSO_4^-$, $CH_3OSO_3^-$, $NO_3^-$, and $EtOSO_3^-$, and (3) each of the side chains having a number of quaternary nitrogen atoms such that each monomer unit has a cationic charge density greater than or equal to two comprising (a) pretreating the natural polysaccharide, if insoluble in water, with an acid solution or, if soluble in water, with an alkaline hydroxide;

(b) dissolving the pretreated polysaccharide of step (a) in water or in an organic solvent and reprecipitating the polysaccharide in amorphous form from the solution;

(c) suspending or dissolving in an organic solvent the precipitated polysaccharide of step (b) and reacting same with aliphatic and/or aromatic amines and/or amino acids having the structure intended to be introduced into the polysaccharide molecules as side chains; and (d) cationizing the polysaccharide side chain(s) by reacting same with quaternary ammonium salts having equal or different nitrogen substituents and having a reactive epoxide or halohydrin group.

3. A process as claimed in claim 2, characterized in that said pretreatment is effected with 0.1-10M hydrochloric, formic or acetic acid for a time of 10-30 hours under reflux.

4. A process as claimed in claim 2, characterized in that said pretreatment is effected with an alkaline hydroxide, having a concentration of 10-30% by weight, at ambient temperature for a time of 1-3 hours.

5. A process as claimed in claim 2, characterized in the organic solvent for dissolving and reprecipitating the pretreated polysaccharide and for the subsequent reactions involved in introducing the side chains into the molecule and their cationization is chosen from the group consisting of aliphatic alcohols with 1-4 carbon atoms; polyalcohols with 2-8 carbon atoms; aliphatic ketones; and linear and cyclic ethers.

6. A process as claimed in claim 2, characterized in that the molar ratio of the glucoside nucleus of the polysaccharide to the cationization agent is between 1:2 and 1:6.

7. A process as claimed in claim 2, characterized in that the steps c) and d) are repeated so as to lengthen the side chains already connected to the glucoside nucleus of the polysaccharide by spacing apart the quaternary nitrogen atoms inserted into a chain by at least three carbon atoms.

* * * * *